United States Patent [19]

Osburn

[11] Patent Number: 4,477,325
[45] Date of Patent: Oct. 16, 1984

[54] SKIN BARRIER COMPOSITION COMPRISING AN IRRADIATED CROSSLINKED ETHYLENE-VINYL ACETATE COPOLYMER AND POLYISOBUTYLENE

[75] Inventor: Frank G. Osburn, Hanover Park, Ill.

[73] Assignee: Hollister Incorporated, Libertyville, Ill.

[21] Appl. No.: 550,020

[22] Filed: Nov. 8, 1983

Related U.S. Application Data

[63] Continuation-in-part of Ser. No. 397,184, Jul. 12, 1982, abandoned.

[51] Int. Cl.$^3$ .................... C08F 8/00; C08L 1/00; A61K 9/70; A61F 5/44
[52] U.S. Cl. ............... 204/159.12; 204/159.14; 204/159.2; 523/105; 523/111; 524/55; 524/521; 525/218; 525/221; 604/336
[58] Field of Search .............. 204/159.12, 159.14, 204/159.2; 523/105, 111; 524/55, 521; 525/218, 221; 604/336

[56] References Cited

U.S. PATENT DOCUMENTS

| | | | |
|---|---|---|---|
| 3,714,096 | 1/1973 | Biale | 525/218 |
| 3,908,658 | 9/1975 | Marsan | 604/336 |
| 3,932,319 | 1/1976 | Clendinning et al. | 524/55 |
| 4,110,290 | 8/1978 | Mori et al. | 428/520 |
| 4,147,831 | 4/1979 | Balinth | 523/111 |
| 4,153,055 | 5/1979 | Estes | 523/111 |
| 4,192,785 | 3/1980 | Chen et al. | 524/55 |
| 4,231,369 | 11/1980 | Sorensen et al. | 604/336 |
| 4,253,460 | 3/1981 | Chen et al. | 604/336 |
| 4,254,008 | 3/1981 | Krsek | 523/118 |
| 4,258,715 | 3/1981 | Goble | 526/230 |
| 4,306,551 | 12/1981 | Hymes | 524/55 |
| 4,338,227 | 7/1982 | Ballard | 525/221 |
| 4,356,819 | 11/1982 | Potaczek | 524/55 |
| 4,359,047 | 11/1982 | Potaczek | 523/111 |
| 4,393,080 | 7/1983 | Pawelchak et al. | 524/55 |

Primary Examiner—Herbert J. Lilling

[57] ABSTRACT

A skin barrier composition is provided which is composed of a mixture of a copolymer resin of ethylene and vinyl acetate (EVA), at least one water absorbing particulate hydrocolloid or polymer, and a water-insoluble dry tack-providing elastomer such as polyisobutylene. The composition after mixing and molding, is subjected to ionizing irradiation to form cross-linked polymer networks of the EVA or EVA with another polymer cross-linking by irradiation. The compositions have exceptional properties for use as barrier sheets, rings, or strips in ostomy, wound drainage, and incontinence devices.

9 Claims, No Drawings

SKIN BARRIER COMPOSITION COMPRISING AN IRRADIATED CROSSLINKED ETHYLENE-VINYL ACETATE COPOLYMER AND POLYISOBUTYLENE

RELATED APPLICATION

This application is a continuation-in-part of copending application Ser. No. 397,184, filed July 12, 1982 and now abandoned.

BACKGROUND AND PRIOR ART

The general field of this invention relates to skin barriers for ostomy, wound drainage, incontinence, and similar uses. For such applications, the barriers are used in the form of molded rings, sheets, or strips, which are applied to protect the skin from the bodily fluid being discharged and to provide a liquid seal. The desirable physical properties of such barrier compositions are diverse, and it has been difficult to achieve all of the desirable properties in combination.

The skin barrier should be soft and flexible, while at the same time providing a degree of elasticity and having the ability to maintain its shape. For initial application, the barrier should have "dry tack", so that the barrier will provide an initial adhesive adherence to the skin. The adhesiveness should also be maintained while the barrier is in contact with an aqueous fluid, such as urine, intestinal or fecal fluids. This is usually referred to as "wet tack".

Skin barriers should also provide mechanical endurance when subjected to bodily fluids. Absorption of the fluid is desirable, but the amount of absorption should be controlled so that undue swelling of the composition does not occur. Excessive swelling can distort the form of the barrier causing it to separate from the skin and break the moisture seal so that the barrier can no longer effectively perform its sealing function. However, if no swelling occurs fluid accumulates between the barrier and the skin and again a separation of the barrier from the skin may occur. Further, penetration of fluid between the barrier and the skin can increase the amount of skin irritation.

Another important consideration is that the barrier should have as long a useful life as possible. This permits the user to leave the barrier in place for a number of days, or in some cases for a week or longer. Moreover, frequent replacement of the barrier increases the cost and inconvenience to the user, and can contribute to irritation of the skin in the area to which the barrier is applied.

For many years there has been a continuing search for improved barrier compositions. One of the early successful compositions was composed of a gelled mixture of karaya gum and glycerin. This composition is still in commercial use, especially in intestinal ostomy applications (viz. ileostomies and colostomies). Such compositions are also used in the form of wound barrier blankets for wound drainage applications, and have been marketed in irradiation-sterilized form for this purpose. However, when karaya is subjected to gamma irradiation, such as for the purpose of sterilization, the irradiation degrades the karaya, decreasing its mechanical strength. To compensate for this effect, in applications where sterilization is important, it has been proposed to incorporate a polyacrylamide resin in the karaya-glycerin formula. See U.S. Pat. Nos. 4,306,551 and 4,307,717. Polyacrylamide resin has also been formulated with glycerin or other polyol, and cross-linked by irradiation, as disclosed in U.S. Pat. No. 4,258,715.

Skin barrier compositions composed of mixtures of elastomers and hydrocolloids are also known, and have been used commercially. See, for example, U.S. Pat. Nos. 3,339,546 and 4,253,460. With this type of barrier composition, the elastomer, which may be a natural or synthetic rubber, or mixtures of such rubbers, comprises the continuous phase, and the hydrocolloid is dispersed therein in particulate form. Both natural hydrocolloid gums such as karaya, pectin, and gelatin, and synthetic hydrocolloids such as carboxymethyl cellulose have been used in varius admixtures. The elastomer such as polyisobutylene provides the compositions with an adhesive dry tack characteristic. The dispersed particles of hydrocolloid absorb water, and also when wet acquire a wet tack adhesive characteristic. Such formulations have been sterilized by gamma irradiation, but such sterilization degrades the polyisobutylene which does not cross-link. Sterilization is thus accomplished at the expense of downgrading desirable physical properties. Such downgrading due to loss of strength by irradiation has tended to limit the marketing of barriers in sterile forms.

SUMMARY OF INVENTION

This invention is based in part on the discovery that skin barrier compositions of superior properties can be prepared by using a cross-linked polymer network with a water-insoluble dry tack-providing elastomer dispersed there through. The polymer network utilizes as a principal ingredient the copolymer resin of ethylene and vinyl acetate (EVA). The EVA may be employed in combination with a lesser amount of a hydrophilic polyacrylamide (AA), or other hydrophilic resin cross-linking with the EVA, or such additional cross-linker may be omitted. In one embodiment, for example, a homogeneous mixture is prepared of the EVA and AA resins and the elastomer such as polyisobutylene. This mixture after being formed into the desired shape is subjected to cross-linking gamma irradiation which forms the polymer network. A minor amount of a hydrocolloid such as karaya is also preferably incorporated. The resulting cross-linked molded product has a combination of properties not heretofore achieved with respect to skin barrier compositions; being soft, flexible, and pliable or stretchable, while providing good mechanical strength. Elastic recovery when distorted from a molded shape may also be achieved. Moreover, the fluid endurance of such formulations is greater than any formulation previously tested. This is especially important in applications where the barrier is in contact with urine, such as urostomy and male incontinence applications. Further the barrier composition can be sterilized by the cross-linking irradiation while at the same time improving the mechanical and fluid endurance properties.

The cross-linked composition can also exhibit controlled swelling while still being adequately water-absorbing and providing satisfactory wet tack. The swelling is limited by the cross-linking with the EVA resin, and by the presence of the continuous elastomer phase. If greater water absorption and wet tack is desired, this can be provided by adding more dispersed particles of a hydrocolloid like karaya, or other water absorbing particulate substance.

DETAILED DESCRIPTION

A principal ingredient of formulations prepared in accordance with this invention is the EVA resin, which is a copolymer of ethylene and vinyl acetate. Where such copolymers contain relatively large amounts of vinyl acetate, they are sometimes also referred to as VAE resins, but for the purpose of this invention the class of such copolymers will be referred to as EVA resins. In general, the EVA resin may contain from 25 to 65% by weight of vinyl acetate the amount of ethylene present being correspondingly from 75 to 35%. In certain embodiments, EVA resins containing relatively large amounts of vinyl acetate are used, such as EVA resins containing from 40 to 60% by weight of vinyl acetate. Suitable EVA resins are available from a number of commercial sources. For example, "ULTRATHENE" and "VYNATHENE" are sold by U.S.I. Chemicals Co., Division of National Distillers and Chemical Corp., New York, N.Y. The VYNATHENE copolymers contain from 40 to 60% vinyl acetate.

In accordance with one embodiment of the present invention, the EVA resin is used in combination with a hydrophilic resin such as polyacrylamide resin which is capable of cross-linking with itself, and/or with EVA to form a polymer network. The polyacrylamide resin may be non-ionic, or may contain cationic or anionic groups. Anionic carboxylic acid groups may be introduced by copolymerizing acrylamide with sodium acrylate, and cationic groups introduced by copolymerizing an acrylamide with beta-methacryloxyethyltrimethylammonium methyl sulfate. Non-ionic, anionic, and catonic acrylamide resins can be used for the purpose of the present invention, but in certain embodiments the cationic acrylamide resins appear to be the most desirable. For example, the acrylamide resins sold as "RETEN" polymers by Hercules Incorporated, Wilmington, Del. can be used. For conciseness such resins will be referred to herein as AA resins. Among the important physical properties provided by the cross-linked network of the EVA and the hydrophilic resin are urine resistance and elastic recovery.

Where the composition is to be irradiated to provide the cross-linked network of the EVA or of the EVA and the AA or other hydrophilic polymer, in certain embodiments from 0.1 to 0.5 parts by weight of the hydrophilic resin or more can be used per part of the EVA resin. In other embodiments, the amount of AA or other hydrophilic resin will range from 0.25 to 0.4 parts by weight per part of the EVA resin. By way of specific example, 31 parts of an EVA resin containing 51% vinyl acetate may be combined with 10 parts of a cationic polyacrylamide resin to produce a cross-linked network.

In embodiments where the cross-linked network is formed of the cross-linked EVA alone, it has been found to be desirable to employ larger proportions of the hydrocolloid, or a mixture of the hydrocolloids, in proportion to the EVA. For example, the EVA may comprise from 10 to 25% by weight of the total formulation, while the hydrocolloid may comprise from 20 to 50% by weight of the formulation. In such embodiments, the polyisobutylene may comprise from about 25 to 55% by weight of the formulation, such as preferably from about 30 to 50%. Instead of polyisobutylene, in certain embodiments, other elastomers can be employed in whole or in part, such as the synthetic rubbers which have heretofore been used in skin barrier compositions.

Such elastomers are water-insoluble, and provide an adhesive, dry tack characteristic. See U.S. Pat. Nos. 3,339,546 and 4,253,460 which further describe suitable elastomers. The elastomer is dispersed in homogeneous admixture with the network forming ingredients. Polyisobutylene is the preferred elastomer, but other elastomers or mixtures of elastomer having similar properties can be used. The amount of elastomer can range from as little as 30% by weight of the total composition up to 65% by weight. A presently preferred range is from 40 to 60% of the composition.

One general formula for compositions of the present invention is:

| Formula A | |
|---|---|
| Ingredients | Parts by Weight |
| EVA copolymer resin | 20 to 50 |
| Hydrophilic cross-linker resin | 3 to 20 |
| Polyisobutylene | 30 to 65 |

Formula A as set out above may be modified by incorporating from 3 to 30 parts by weight of dispersed particles of a water-absorbing wet tack-providing hydrocolloid or other water-absorbing particulate substance providing a wet tack characteristic. The hydrocolloid may be a natural vegetable hydrocolloid gum, or mixtures of such gums, such as karaya, gelatin, pectin, guar, etc. Synthetic hydrocolloids such as sodium carboxymethyl cellulose can be used but are less desirable. Natural hydrocolloids are especially suitable for purposes of the present invention.

A formula incorporating the four ingredients described above is:

| Formula B | |
|---|---|
| Ingredients | Parts by Weight |
| EVA copolymer resin | 25 to 35 |
| Hydrophilic cross-linker resin | 5 to 15 |
| Polyisobutylene | 40 to 60 |
| Hydrocolloid | 5 to 15 |

In certain embodiments the cross-linked polymer network is provided entirely by the EVA, a representative general formula is as follows:

| Formula C | |
|---|---|
| Ingredients | Parts by Weight |
| EVA copolymer resin | 10 to 30 |
| Polyisobutylene | 30 to 50 |
| Hydrocolloid | 20 to 50 |

For example, in specific embodiments of the above formula, the EVA may contain about equal parts by weight of ethylene and vinyl acetate, and the hydrocolloid may be a mixture of hydrocolloids, such as gelatin, pectin, and sodium carboxymethyl cellulose.

In the manufacture of compositions of this invention mixtures of the foregoing ingredients can be prepared in a known manner, such as the procedures described in U.S. Pat. Nos. 3,339,546 and 4,253,460. Roll mills, banbury mixers, and similar mixing apparatus can be used to blend the ingredients. The mixing should be continued until a substantially uniform or homogeneous mixture is obtained.

More specifically, the polyacrylamide resin, if used, and the hydrocolloid gum will usually be in the form of dry powders. These can be first dry blended to form a dry mix for later addition to the other ingredients. The elastomer and the EVA resin are first combined in a kneading-type mixer (or other suitable mixer), and are mixed to substantial homogeneity. The mixing is then continued with the slow addition of the dry powder blend. Mixing is continued until a substantially homogeneous final mixture is obtained. The mixture thus prepared may be stored for later use in preparing the molded products.

The thus prepared mixture may be formed into the desired shape (strip, ring, square, etc.) by any number of the means commonly used for converting plastics and elastomers to such shapes. These means include compression molding and injection molding. Calendering and extrusion of the mixture in sheet form, followed by die cutting into the desired shape may also be used. The latter procedure has manufacturing advantages for producing products from formed sheets.

With compositions of this invention, improved properties are obtained by subjecting the compositions to cross-linking irradiation. A source of ionizing radiation is used, as described in U.S. Pat. No. 4,115,339 for cross-linking high molecular weight vinyl polymers. For example, a Cobalt-60 radiation source can be used to provide suitable ionizing gamma irradiation. The level of radiation is not highly critical but is selected to obtain a satisfactory degree of cross-linking without excessive degradation of the elastomer and the hydrocolloid. In general, this can be accomplished within the range from 0.2 to 8.0 megarads. A presently preferred range is from about 2 to 4 megarads. Lower levels of irradiation can be used to obtain a lesser degree of cross-linking which may be desirable in certain products. At radiation levels of about 2.8 megarads and higher sterilization can also be obtained.

The practice of the present invention in specific and the results obtained thereby are illustrated by the following examples.

EXAMPLE I

In an illustrative embodiment, a skin barrier composition is prepared in accordance with the following formula:

| Formula I | |
|---|---|
| Ingredients | Weight % |
| EVA copolymer resin | 31.0 |
| AA resin | 10.0 |
| Polyisobutylene | 48.0 |
| Gum karaya powder | 11.0 |
| | 100.0 |

With reference to Formula I, as set out above, the EVA copolymer resin may contain from 45 to 55% vinyl acetate. For example, the EVA resin may be VYNATHENE EY 905 resin (51% vinyl acetate) of U.S. Industrial Chemicals Co., Division of National Distillers & Chemical Corp., New York, N.Y. The AA resin may be a cationic acrylamide resin, such as RETEN 210P resin of Hercules Incorporated, Wilmington, Del. The polyisobutylene may be obtained from Exxon Chemical Co., Elastomer Dept., Houston, Tex., as "VISTANEX" Grade LM-MH, or Grade LM-MS, or the "OPPANOL" products (B-10 to B-18) of BASF Wyandotte Corp., Holland, Mich. Such polyisobutylenes have a viscosity average molecular weight within the range from about 36,000 to 58,000 (Flory). The gum karaya powder is preferably in finely divided form, such as smaller than about 140 mesh, and containing from about 10 to 18% moisture.

Compounding and Forming

As a specific example of compounding, the ingredients of Formula A, the AA resin and the gum karaya, both being in powder form, are mixed to produce a dry blend. A ribbon blender or other powder mixer can be used for this purpose. Using a kneading-type or comparable mixer, the polyisobutylene is mixed for approximately one minute, the EVA resin is added, and mixing is continued for about five minutes. The dry blend is then added incrementally while mixing is continued and until all of the powder has been uniformly dispersed in the other ingredients. The completed homogeneous mixture is then discharged and formed into loaves for further processing. The loaves may be stored on trays until ready for use in forming the molded products.

The foregoing compositions and other compositions of this invention may be formed into sheets by passing the material through a calender having a pre-set gap, or the sheets may be formed by compression in a mold cavity of the desired depth. The composition may also be formed by passing the mixed material through conventional extrusion equipment equipped with a slot or tape die set to extrude a ribbon of approximately the desired thickness. If necessary the extruded ribbon can be further compressed in thickness by passing it through one or more sets of compression rollers. The currently preferred mode of preparation consists of extruding a ribbon of the desired width and thickness directly onto release paper, which is then cut into stock "preforms". If desired, the preforms can be covered, on their exposed sides, with one of several types of backings, either porous or non-porous films being used. Among the available backings, it is preferable to use a plastic film, porous or non-porous, with or without a contact adhesive; non-woven as well as woven fabrics; porous or non-porous types of contact adhesive backed tapes. The backings may be applied by hand or in conjunction with the compression rollers referred to above.

The completed products are then packaged in suitable sealed containers such as plastic envelopes. The packaging material is desirably selected so that the product can be irradiated after packaging to provide the cross-linking and sterilization described above. For example, Mylar is a suitable flexible packaging material. Irradiation is then carried out at a level of around 2.5 to 3.0 megarads to cross-link the resins, and from about 2.8 megarads and above to also sterilize the product.

Properties

Skin barrier products manufactured as described herein provide a remarkable combination of properties. The molded products in the form of sheets, strips, rings, and the like are soft, stretchable and exhibit better elastic recovery than any previously known products of this kind. The outstanding properties of stretchability and elastic recovery are particularly evident when the composition is in the form of thin sheets or strips. These properties are believed to be due to the cross-linked polymer network which provides the soft elastomer with structural coherence. The products also provide good dry tack and wet tack properties, and controlled water absorbency. The endurance of these products in contact with degradative fluids such as urine and intestinal fluid far surpasses the best prior compositions for ostomy, wound drainage, and incontinence uses. The fluid endurance to urine is illustrated by the following examples.

Endurance Tests

Formula I compositions before and after irradiation were subject to a urine endurance test. The procedure used was as follows: A simulated urine was prepared as described in *Remington's Pharmaceutical Sciences*, "Urine", pg. 598–9, Ed 15 (1975). The endurance test apparatus including a tank for containing the simulated urine, and a plurality of tripod testing fixtures, which may be placed in the tank in contact with the solution. The tank was provided with a heater and thermostat control for maintaining the urine solution at a selected temperature, which for this comparison was 38° C. The testing fixture has a platform at the top with a sample-receiving recess. The center portion of the recess is cut-out to provide an opening through the platform. When placed in test position, the test samples bridge the openings. U-shaped weights are then placed over the samples. These weights are in the form of steel hooks weighing approximately 7.4 grams. In use, the hooks are placed over the samples so that when the hooks break through the samples they would fall freely through the openings in the platforms. Nylon strings are attached to the upper cross-arm portions of the inverted U-shaped hooks and the strings are attached to the operating levers of micro switches, the lengths of strings being selected so that when the sample is broken, the micro switch will be activated, and a timing clock for the particular sample will be stopped. In starting the test, after the samples have been placed in the tank and the strings attached to the microswitch levers, the simulated urine is added to the tanks to a level above the position of the samples, and the timing clocks for each sample are started. The elapsed time for breakthrough of each sample is thereby automatically recorded.

The samples for the endurance test were die cut using a steel rule die to a size of 28×10>1.5 mm. The center portions of the samples were engaged by the weighted hooks. The measured time for breakthough was corrected by multiplying the measured time by 1.0 grams of the sample divided by actual weight of the sample.

TABLE A

| Endurance to Simulated Urine | |
|---|---|
| Description of Samples | Endurance Time (hrs.)[a] |
| Formula A before irradiation | less than 72 |
| Formula A after irradiation | over 780 |

[a] Averages of the actual times of multiple runs.

EXAMPLE II

In a presently preferred formulation for use as a sterile ostomy barrier, the ingredients are combined according to the following formula:

| Formula II | |
|---|---|
| Ingredients | Weight % |
| Polyisobutylene | 39.0 |
| EVA copolymer resin (51% ethylene) | 21.0 |
| Gelatin | 18.6 |
| Pectin | 11.8 |
| Sodium carboxymethyl cellulose | 9.6 |
| | 100.0 |

As will be noted, in the above formula, a mixture of three hydrocolloids is employed, the total of the hydrocolloids present in the mixture being 40% of the formulation. All of the hydrocolloids are used in particulate, finely-divided condition. Approximately two parts of the hydrocolloid by weight are present per part of the EVA, and approximately equal amounts of hydrocolloids with the polyisobutylene. The ingredients are combined in the manner previously described, and after molding, the molded composition is irradiated at a level of about 2 to 3 megarads. The irradiation sterilizes the composition and forms a cross-linked polymer network from the EVA.

Where it is desired to provide greater water absorbency, a minor amount of a particulate polymer of high water absorbency can be included, such as a starch polyacrylonitrile graft copolymer. Such polymers may be formed from granule starch as described in U.S. Pat. No. 3,661,815, or from gelatinized starch using either an acrylonitrile monomer, as described in U.S. Pat. No. 3,997,484, or a mixture of acrylonitrile monomer with other acrylic comonomer as described in U.S. Pat. No. 4,134,863. Highly water absorbing synthetic polymers can also be employed.

In general, the particulate water absorbing polymer should be capable of absorbing at least 50 times its own weight of distilled water, and such polymers are available which absorb over 200 times their weight of distilled water. The formulas set out above may therefore be modified by incorporating from 1 to 20% by weight (based on the total formula) of a highly water absorbing particulate polymer, such as, preferably, from about 5 to 15% by weight based on the total composition.

When the water absorbing polymer is used, the amount of hydrocolloid may be reduced, or in some cases, entirely eliminated. The degree of water absorption can thereby be controlled by increasing or decreasing the amount of hydrocolloid and/or water-absorbing polymer. Further, as the amount of the cross-linked EVA is increased, the degree of water absorption will tend to be reduced. Therefore, for example, when it is desired to reduce water absorbency, the amount of EVA can be increased and the amount of hydrocolloid and/or water absorbing polymer can be correspondingly reduced.

I claim:
1. The method of manufacturing a skin barrier composition, in the form of a molded shape, comprising:
    (a) preparing a homogeneous solid phase mixture by mixing as solid ingredients an uncrosslinked elastomeric copolymer of ethylene and vinyl acetate (EVA) with polyisobutylene, and at least one water-absorbing particulate hydrocolloid or polymer;
    (b) forming said mixture into molded shapes applicable to the skin; and
    (c) subjecting said molded shapes to form 0.2 to 8.0 megarads of gamma irradiation to crosslink the EVA polymer.
2. The molded shapes for application to the skin produced by the method of claim 1.

3. The method of claim 1 in which said EVA contains from 40 to 60% by weight of vinyl acetate.

4. The method of claim 1 in which said mixture also contains an acrylamide polymer (AA), from 0.25 to 0.4 parts by weight of said AA polymer being used per part of said EVA copolymer.

5. The method of manufacturing a skin barrier composition in the form of molded shapes, comprising:
   (a) preparing a homogeneous solid phase mixture by mixing as solid ingredients an uncrosslinked elastomeric copolymer of ethylene and vinyl acetate (EVA), polyisobutylene, and a hydrocolloid or mixture of hydrocolloids, said EVA containing from 40 to 60% by weight of vinyl acetate;
   (b) forming said mixture into molded shapes applicable to the skin; and
   (c) subjecting said molded shapes to from 2 to 4 megarads of gamma irradiation to crosslink the EVA.

6. The molded shapes for application to the skin produced by the method of claim 5.

7. The method of manufacturing a skin barrier composition in the form of molded shapes, comprising:
   (a) preparing a solid phase homogeneous mixture by mixing as solid ingredients the following:

| Ingredients | Parts by Weight |
   | --- | --- |
   | EVA copolymer resin | 10 to 30 |
   | polyisobutylene | 30 to 50 |
   | hydrocolloid | 20 to 50 | said EVA copolymer being an uncrosslinked copolymer of ethylene and vinyl acetate containing from 25 to 65% by weight of vinyl acetate, said hydrocolloid comprising a particulate water-absorbng, wet-tack-providing vegetable hydrocolloid gum;
   (b) forming said mixture into molded shapes applicable to the skin;
   (c) packaging said molded shapes in containers within which the molded shapes can be subjected to gamma irradiation; and
   (d) subjecting said packaages to from 0.2 to 8.0 megarads of gamma irradiation to crosslink the EVA.

8. The method of claim 7 in which said mixture also contains from 1 to 20% by weight of an acrylonitrile-starch graft copolymer.

9. The packaged irradiated molded shapes produced by the method of claim 8.

* * * * *